United States Patent

Nelson et al.

Patent Number: 6,127,380
Date of Patent: Oct. 3, 2000

[54] 4-AMINOALKOXY-1H-BENZOIMIDAZOLES

[75] Inventors: James Albert Nelson, Washington Crossing, Pa.; Richard Eric Mewshaw, Princeton, N.J.

[73] Assignee: American Home Products Corporation, Madison, N.J.

[21] Appl. No.: 09/024,845

[22] Filed: Feb. 17, 1998

Related U.S. Application Data

[60] Provisional application No. 60/038,681, Feb. 18, 1997.

[51] Int. Cl.[7] ............... C07D 235/02; C07D 401/02; A61K 31/415; A61K 31/47
[52] U.S. Cl. .............. 514/307; 514/314; 514/394; 546/148; 546/152; 548/306.4
[58] Field of Search ................... 546/148, 152; 548/306.4; 514/307, 394, 314

[56] References Cited

U.S. PATENT DOCUMENTS

| 5,958,965 | 9/1999 | Mewshaw et al. ............. 514/415 |

FOREIGN PATENT DOCUMENTS

| 0237781 | 9/1987 | European Pat. Off. . |
| 0707007 | 4/1996 | European Pat. Off. . |
| 3830060 | 3/1990 | Germany . |
| 60-226810 | 11/1985 | Japan . |
| 9500509 | 5/1995 | Japan . |
| WO9723216 | 7/1997 | WIPO . |
| WO9808817 | 3/1998 | WIPO . |

OTHER PUBLICATIONS

Jaen J.C. et al., Journal of Med. Chem., vol. 31, No. 8 (Aug. 1988) pp. 1621–1625.

Primary Examiner—Zinna Northington Davis
Attorney, Agent, or Firm—Rebecca R. Barrett

[57] ABSTRACT

This invention relates to $D_2$ dopaminergic compounds of the formula

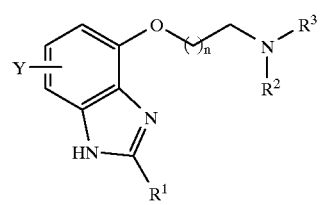

wherein:

$R^1$ is hydrogen, trifluoromethyl, pentafluoroethyl, heptafluoropropyl, straight-chain or branched alkyl group having up to 6 carbons or benzyl optionally substituted by one to three substituents selected from halogen, amino, nitro, hydroxy, and $C_1$–$C_6$ alkoxy;

$R^2$ is hydrogen or $C_1$–$C_6$ alkyl;

$R^3$ is hydrogen, straight-chain or branched alkyl group having up to 10 carbon atoms, cyclohexylmethyl, —$(CH_2)_m$Ar where Ar is phenyl, naphthalenyl, thienyl, furanyl, or pyridinyl, each optionally substituted by one to two substituents selected from halogen, $C_1$–$C_6$ alkoxy, trifluoromethyl and $C_1$–$C_6$ alkyl, and m is 1–3 or $NR^2R^3$ is 1,2,3,4-tetrahydroquinolin-1-yl or 1,2,3,4-tetrahydroisoquinolin-2-yl;

Y is hydrogen, halogen, lower alkyl, amino, or lower alkoxy;

n is 1–5:

or a pharmaceutically acceptable salt thereof. These $D_2$ dopaminergic compounds are useful in the treatment of schizophrenia, Parkinson's disease, Tourette's syndrome, and drug or alcohol addiction.

26 Claims, No Drawings

4-AMINOALKOXY-1H-BENZOIMIDAZOLES

This application claims benefit of priority of provisional patent application 60/038,681 filed Feb. 18, 1997.

FIELD OF INVENTION

This invention relates to 4-(aminoalkoxy)-1H-benzoimidazoles which have dopamine $D_2$ agonist activity and thus are useful in the treatment of schizophrenia, Parkinson's disease, Tourette's syndrome and drug or alcohol addiction.

BACKGROUND OF THE INVENTION

Efforts to induce antipsychotic activity with dopamine autoreceptor agonists have been successful (Dorsini I *Adv. Biochem. Psychopharmacol.*, 16, 645–648, 1977; Tamminga et al., *Science*, 200, 567–568, 1975; and Tamminga et al., *Psychiatry*, 398–402, 1986). A method for determining intrinsic activity at the dopamine $D_2$ receptor was recently reported (Lahti et al., *Mol. Pharm.*, 42, 432–438, 1993) Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

In accordance with this invention, there is provided a group of compounds which are useful antipsychotic agents. The compounds of this invention are dopamine agonists various degrees of intrinsic activity some of which are selective autoreceptor agonists, and therefore partial agonist (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing a well as inhibition of dopamine synthesis and release and therefore provide a means of controlling hyperactivity of the dopaminergic systems. The compounds of this invention were also found to have high intrinsic activity and therefore they can behave as the natural neurotransmitter i.e. as full agonists. As such, they are useful in the treatment of diseases having abnormal concentrations of dopamine could be used as dopamine surrogates possibly in the treatment of Parkinson's disease. The compounds of this invention are essentially free from extrapyramidal side effects (EPS).

DESCRIPTION OF THE PRIOR ART

A number of compounds structurally related to the compounds of this invention are claimed in prior art.

JP 02306916A claims a class of benzazole compounds of the formula below, where X is

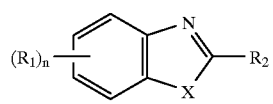

S or N, which are inhibitors of platelet adhesion for the treatment of arteriosclerosis, ischemic heart diseases, chronic arterial obstruction, and acute or chronic nephritis. In the above formula, $R_1$ includes $—(O—A)_m—NR^4R^5$ where A is lower alkylene, m is 0 or 1, $R^4$ and $R^5$ include hydrogen, phenyl(lower)alkyl, or $NR^4R^5$ is a 5–6 membered saturated or unsaturated heterocycle and $R_2$ includes phenyl optionally substituted by 1–3 substituents selected from optionally halogenated lower alkoxy, lower alkyl, hydroxy, halogen or aminoalkoxy.

DE 3830060 claims a class of 2-Arylbenzimidazole erythrocyte aggregation inhibiting compounds of the following formula

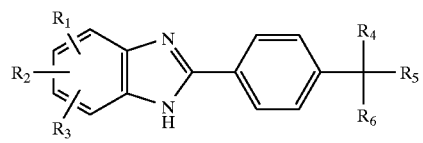

where $R^4$ is methyl, cyano, carboxamido or aminomethyl, $R^5$ is H or alkyl, $R^6$ is alkyl or cycloalkyl or $R^5$ and $R^6$ completes a cyclohexane ring which are useful for the treatment of circulatory disorders and shock.

SUMMARY OF THE INVENTION

The compounds of this invention are depicted by the following Formula I:

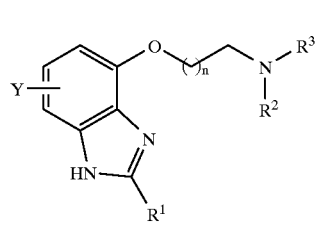

wherein:
  $R^1$ is hydrogen, trifluoromethyl, pentafluoroethyl, heptafluoropropyl, straight-chain or branched alkyl group having up to 6 carbons or benzyl optionally substituted by one to three substituents selected from halogen, amino, nitro, hydroxy, and $C_1$–$C_6$ alkoxy;
  $R^2$ is hydrogen or $C_1$–$C_6$ alkyl;
  $R^3$ is hydrogen, straight-chain or branched alkyl group having up to 10 carbon atoms, cyclohexylmethyl, $—(CH_2)_m$Ar where Ar is phenyl, naphthalenyl, thienyl, furanyl, or pyridinyl, each optionally substituted by one to two substituents selected from halogen, $C_1$–$C_6$ alkoxy, trifluoromethyl and $C_1$–$C_6$ alkyl, and m is 1–3 or $NR^2R^3$ is 1,2,3,4-tetrahydroquinolin-1-yl or 1,2,3,4-tetrahydroisoquinolin-2-yl;
  Y is hydrogen, halogen, lower alkyl, amino, or lower alkoxy;
  n is 1–5:
  and the pharmaceutically acceptable salts thereof.

The pharmaceutically acceptable acid addition salt having the utility of the free base are prepared by methods well known to the art with both inorganic or organic acids, including but not limited to fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, paminobenzoic, glutamic, benzene-sulfonic, hydrochloric hydrobromic, sulfuric, cyclohexylsulfamic, phosphoric and nitric acids.

The compounds of Formula III, where $R^1$ is hydrogen, can be prepared by the overall sequence as follows:

Scheme I

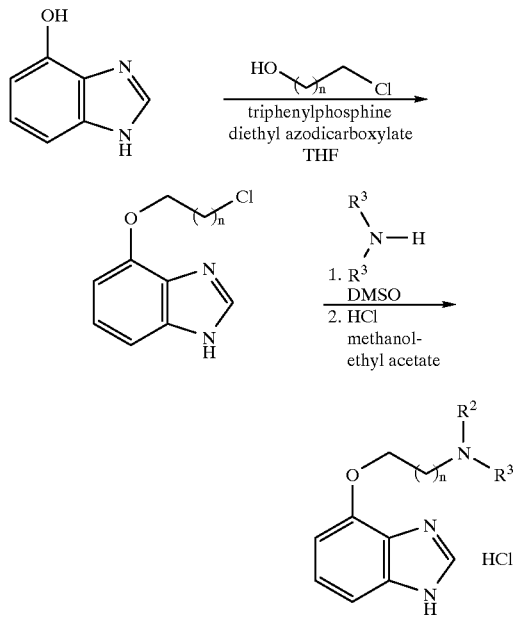

The compounds of Formula III, where $R_1$ is not hydrogen, can be prepared by the overall sequence as follows:

Scheme II

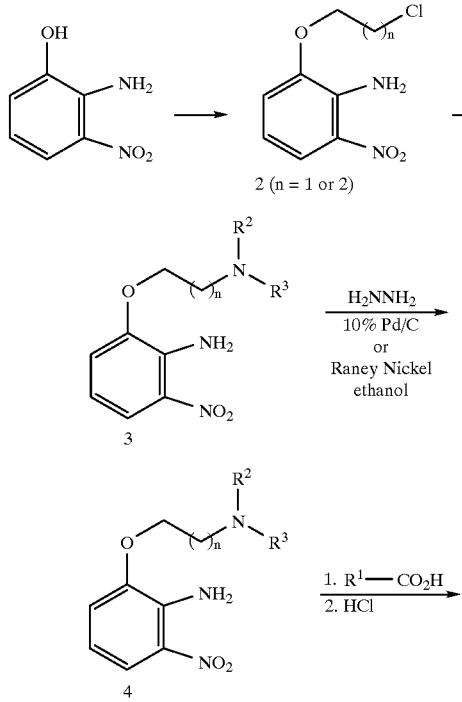

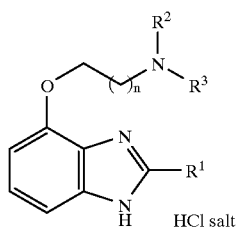

The compounds of Formula III, where $R_2$ is hydrogen, the secondary amine can be protected by a trifluoroacetyl group prepared by the overall sequence as follows:

Scheme III

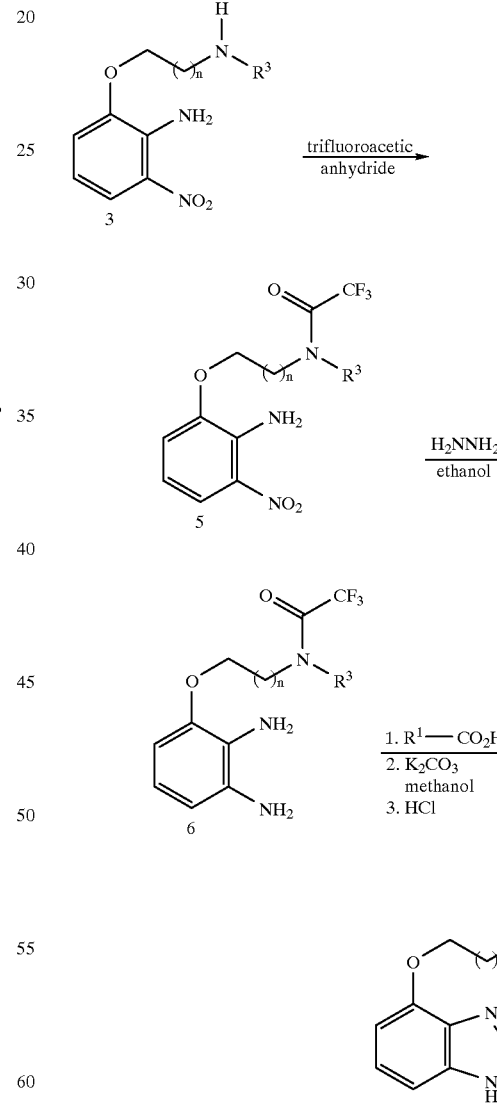

An intermediate for compounds of Formula III where Y is halogen can be prepared by the following sequence:

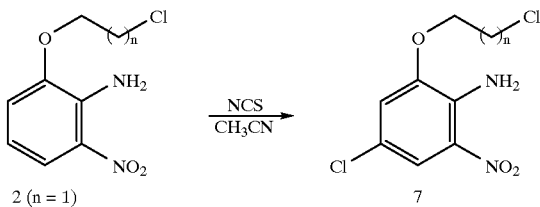

Specific exemplification of the production of representative compounds of this invention is given in the following procedures:

Intermediate 1

4-(2-Chloroethoxy)-benzimidazole

To a solution of 4-hydroxybenzimidazole (3.1 g, 32.4 mmol), triphenylphosphine (12.75 g, 48.6 mmol) and 2-chloroethanol (5.2 g, 64.8 mmol) in tetrahydrofuran (75 mL) at 0–5° C. was added over 30 min a solution of diethyl azodicarboxylate (8.5 g, 48.7 mmol) in tetrahydrofuran (75 mL). The mixture was warmed to 23° C. and stirred for 48 hr. The solvent was removed under vacuum to give a dark brown oil. Purification by chromatography (silica gel, ethyl acetate-1% 2M $NH_3$ in methanol) afforded 2.9 g (63.8%) of a solid residue that was crystallized from ethyl acetate to give the title compound as a white solid, mp 153–154° C.

Elemental analysis for $C_9HClN_2O$: Calc'd: C, 54.97; H, 4.61; N, 14.25 Found: C, 54.86; H, 4.38; N, 14.26

Intermediate 2a (n=1)

2-(2-Chloro-ethoxy)-6-nitro-phenylamine

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 mL) was refluxed for 24 hr. The mixture was cooled, filtered and the solids were washed with ethyl acetate. The filtrate was concentrated to an oily residue that was dissolved in ethyl acetate (500 mL). The organic layer was washed with 1 N sodium hydroxide (250 mL), water (500 mL), and brine (2X 500 mL), dried over anhydrous magnesium sulfate. Concentration of the filtered solution and trituation of the residue with hexane afforded 37.8 g (84.6%) of product as an orange solid, mp 71–73° C.; MS (+)PBEI m/e 216/218 ($M^+$).

Elemental analysis for $C_8H_9ClN_2O_3$: Calc'd: C, 44.36; H, 4.19; N, 12.93 Found: C, 44.45; H, 4.02; N, 12.97

Following this general procedure above utilizing 1,3-dibromopropane afforded intermediate 2b, 2-(3-bromo-propoxy)-6-nitro-phenylamine, as a yellow solid, (78.7%) mp 88–89° C.; MS EI m/e 274/276 $[M^+]$.

Elemental analysis for $C_9H_{11}BrN_2O_3$: Calc'd: C, 39.29; H, 4.03; N, 10.18 Found: C, 39.71; H, 3.91; N, 10.27

Intermediate 3a 2-(2-Benzylamino-ethoxy)-6-nitro-phenylamine

A mixture of 2-(2-chloroethoxy)-6-nitrophenylamine (2a, 3.0 g, 13.8 mmol) and benzylamine (9.0 g, 84.0 mmol) was heated at 100–110° C. for 6 hr. The excess benzylamine was removed by distillation under vacuum (70–75° C./0.1 mm). The residue was poured into 1 N sodium hydroxide (300 mL) and extracted with ethyl acetate (2X, 300 mL). The combined organic layer was washed with water (2X, 300 mL) and brine (300 mL). The ethyl acetate layer was dried over anhydrous magnesium sulfate, filtered, and the solvent removed under vacuum to give 5.1 g of crude red oil. Purification by chromatography (500 g silica gel, ethyl acetate: 2 M $NH_3$ in methanol, 20:1) afforded 3.54 g (89.3%) of a red semi-solid, mp 33–60° C.; MS EI m/e 287 ($M^+$).

Elemental analysis for $C_{15}H_{17}N_3O_3$: Calc'd: C, 62.71; H, 5.96; N, 14.62 Found: C, 62.64; H, 6.04; N, 14.23

This general procedure utilizing 4-methyl-benzylamine, thiophene-2-methylamine, 1-naphthalenemethylamine, 1,2, 3,4-tetrahydroisoquinoline afforded:

3b 2-[2-(4-Methyl-benzylamino)-ethoxy]-6-nitro-phenylamine as a yellow solid (89.0%): mp 55–57° C.; MS EI m/e 301 ($M^+$).

Elemental analysis for $C_{16}H_{19}N_3O_3$: Calc'd: C, 63.77; H, 6.36; N, 13.94 Found: C, 63.32; H, 6.37; N, 13.82

3c 2-Nitro-6-{2-[(thiophen-2-ylmethyl)-amino]-ethoxy}-phenylamine as a red semi-solid material (88.5%).

Elemental analysis for $C_{13}H_{15}N_3O_3S$: Calc'd: C, 53.23; H, 5.15; N, 14.32 Found: C, 52.86; H, 4.93; N, 14.15

3d 2-{2-[(Naphthalen-1-ylmethyl)-amino]-ethoxy}-6-nitrophenylamine as a yellow solid (76.3%), mp 66–67° C.; MS EI m/e 337 ($M^+$).

Elemental analysis for $C_{19}H_{19}N_3O_3$: Calc'd: C, 67.64; H, 5.68; N, 12.45 Found: C, 67.20; H, 5.66; N, 12.26

3e 2-[2-(3,4-Dihydro-1H-isoquinolin-2-yl)-ethoxy]-6-nitro-phenylamine as a yellow solid (87.1%), mp 95–96° C.; MS EI m/e 313 ($M^+$).

Elemental analysis for $C_{17}H_{19}N_3O_3$: Calc'd: C, 65.16; H, 6.11; N, 13.41 Found: C, 64.87; H, 6.11; N, 13.40

This general procedure utilizing 2-(3-bromo-propoxy)-6-nitro-phenylamine (2b, n=2) and benzylamine afforded:

3f 2-(3-Benzylamino-propoxy)-6-nitro-phenylamine as a viscous orange oil (85.5%); MS EI m/e 301 ($M^+$).

Elemental analysis for $C_{16}H_{19}N_3O_3$: Calc'd: C, 63.77; H, 6.36; N, 13.94 Found: C, 63.66; H, 6.28; N, 13.89

This general procedure utilizing 4-chloro2-(2-chloro-ethoxy)-6-nitro-phenylamine (7) and benzylamine, 4-chloro-benzylamine afforded:

3g 2-(2-Benzylamino-ethoxy)-4chloro-6-nitro-phenylamine as a orange-brown colored solid (54.0%), mp 87–88° C.; %); MS EI m/e 321/323 ($M^+$).

Elemental analysis for $C_{15}H_{16}ClN_3O_3$: Calc'd: C, 55.99; H, 5.01; N, 13.06 Found: C, 55.85; H, 4.90; N, 13.13

3h 2-[2-(4-Chloro-benzylamino)-ethoxy]-4-chloro-6-nitro-phenylamine as an orange-brown colored solid (83.0%), mp 116–118° C.

Elemental analysis for $C_{13}H_{15}Cl_2N_3O_2$: Calc'd: C, 50.58; H, 4.24; N, 11.80 Found: C, 50.65; H, 4.13; N, 11.51

3i 2-[2-(4-Fluoro-benzylamino)-ethoxy]-6-nitro-phenylamine as an orange solid (89.8%), mp 72–74° C.

Elemental analysis for $C_{15}H_{16}FN_3O_3$: Calc'd: C, 59.01; H, 5.28; N, 13.76 Found: C, 58.92; H, 5.16; N, 13.71

3j 2-Nitro-6-[2-(4-trifluoromethyl-benzylamino)-ethoxy]-phenylamine as an orange solid (86.7%), mp 64–66° C.

Elemental analysis for $C_{16}H_{16}F_3N_3O_3$: Calc'd: C, 54.09; H, 4.54; N, 11.83 Found: C, 53.99; H, 4.33; N, 11.74

3k 2-Nitro-6-[2-(3-phenyl-propylamino)-ethoxy]-phenylamine quarter hydrate as a viscous orange oil (83.4%); MS EI m/e 315 ($M^+$).

Elemental analysis for $C_{17}H_{21}N_3O_3$ 0.25 $H_2O$: Calc'd: C, 63.83; H, 6.78; N, 13.14 Found: C, 63.90; H, 6.56; N. 13.07

Intermediate 4a 3-(2-Benzylamino-ethoxy)-benzene-1,2-diamine

To a mixture containing 2-(2-benzylamino-ethoxy)-6nitro-phenylamine (3a, 0.5 g, 1.74 mmol), 10% palladium on carbon (0.1 g) in ethanol (20 mL) was slowly added a solution of hydrazine hydrate (0.6 mL) in ethanol (6.0 mL). The mixture was heated to 55–60° C. and stirred at that temperature for 16 hr. The mixture was cooled to 25° C., filtered and the catalyst was washed with ethanol. The filtrate was concentrated under vacuum and the residue was diluted with ethyl acetate (100 mL). The organic layer was washed with water (2X, 100 mL) and brine (100 mL), dried over anhydrous magnesium sulfate, filtered, and the solvent removed under vacuum to give 0.38 g (85.5% crude yield) of product as a brown viscous oil. This material was not purified further, but used immediately in the next step.

This general procedure utilizing 2-[2-(4-methyl-benzylamino)-ethoxy]-6-nitro-phenylamine (3b), 2-nitro-6-{2-[(thiophen-2-ylmethyl)-amino]ethoxy}-phenylamine (3c), 2-{2-[(naphthalen-1-ylmethyl)-amino]-ethoxy}-6-nitro-phenylamine (3d), 2-[2-(3,4-dihydro-1H-isoquinolin-2-yl)-ethoxy]-6-nitro-phenylamine (3e), and 2-(3-benzylamino-propoxy)-6-nitro-phenylamine (3f) afforded:

4b 3-[2-(4-Methyl-benzylamino)-ethoxy]-benzene-1,2-diamine as a off-white solid (79.4%), mp 77–79° C.; MS EI m/e 271 (M$^+$).

Elemental analysis for $C_{16}H_{21}N_3O$: Calc'd: C, 70.82; H, 7.80; N, 15.49 Found: C, 70.53; H, 7.89; N, 15.50

4c 3-{2-[(Thiophen-2-ylmethyl)-amino]-ethoxy}-benzene-1,2-diamine as an amber-colored oil (70.0%); MS EI m/e 263 (M$^+$).

4d 3-{2-[(Naphthalen-1-ylmethyl)-amino]-ethoxy}-benzene-1,2-diamine quarterhydrateas a black oil (82.0%); MS EI m/e 307 (M$^+$).

Elemental analysis for $C_{19}H_{21}N_3O \cdot 0.25 H_2O$: Calc'd: C, 73.17; H, 6.95; N, 13.47 Found: C, 73.29; H, 6.86; N, 13.30

4e 3-[2-(3,4-Dihydro-1H-isoquinolin-2-yl)-ethoxy]-benzene-1,2-diamine as a solid (95%), mp 76–77° C. This material was characterized as the dihydrochloride 0.4 H$_2$O salt; MS EI m/e 283 (M$^+$).

Elemental analysis for $C_{17}H_{21}N_3O \cdot 2 HCl \cdot 0.4 H_2O$: Calc'd: C, 56.17; H, 6.60; N, 11.56 Found: C, 56.15; H, 6.68; N, 11.25

4f 3-(3-Benzylamino-propoxy)-benzene-1,2-diamine as an amber-colored oil; MS EI m/e 271 (M$^+$).

Elemental analysis for $C_{16}H_{21}N_3O \cdot 0.3 H_2O$: Calc'd: C, 69.44; H, 7.87; N, 15.18 Found: C, 69.47; H, 7.82; N, 15.30

This general procedure utilizing 2-[2-(4chloro-benzylamino)-ethoxy]-4-chloro-6-nitro-phenylamine (3h) and Raney nickel in place of 10% Pd/C afforded:

4g 3-[2-(4-chloro-benzylamino)-ethoxy]-4-chloro-benzene-1,2-diamine as a light-tan colored solid (75.0%), mp 109–110° C.

Elemental analysis for $C_{15}H_{17}Cl_2N_3O$: Calc'd: C, 55.23; H, 5.25; N, 12.88 Found: C, 55.04; H, 5.09; N, 12.62

4h 3-[2-(4-Fluoro-benzylamino)-ethoxy]-benzene-1,2-diamine as a white solid (82.4%), mp 70–71° C.

Elemental analysis for $C_{15}H_{18}FN_3O \cdot 0.1 H_2O$: Calc'd: C, 65.12; H, 6.62; N, 15.16 Found: C, 64.94; H, 6.52; N, 14.93

4i 3-[2-(4-Trifluoromethyl-benzylamino)-ethoxy]-benzene-1,2diamine as a white solid (87.2%), mp 94–95° C.

Elemental analysis for $C_{16}H_{18}F_3N_3O$: Calc'd: C, 59.07; H, 5.58; N, 12.92 Found: C, 58.93; H, 5.24; N, 12.78

4j 3-[2-(3-phenyl-propylamino)-ethoxy]-benzene-1,2-diamine as an oil (76.2%); MS (+)FAB m/e 286 (M+H$^+$).

Intermediate 5a

N-[2-(2-Amino-3-nitro-phenyoxy)-ethyl]-N-benzyl-2,2,2-trifluoro-acetamide

To a solution containing 2-(2-benzylamino-ethoxy)-6-nitro-phenylamine (3a, 0.50 g, 1.74 mmol), triethylamine (0.50 mL) and methylene chloride (10 mL) was slowly added trifluoroacetic acid anhydride (0.32 mL, 2.26 mmol). After 2 hr, the reaction mixture was poured into 1 N sodium hydroxide (50 mL) and extracted with methylene chloride. The organic layer was washed with water (2X, 50 mL) and brine (50 mL), dried over anhydrous magnesium sulfate, filtered, and the solvent removed under vacuum to give a crude yellow residue. Crystallization of this material from ethyl acetate-hexane afforded 0.55 g (81.7%) of a yellow solid, mp 134–135° C.; MS EI m/e 383 (M$^+$).

Elemental analysis for $C_{17}H_{16}F_3N_3O_4$: Calc'd: C, 53.27; H, 4.21; N, 10.96 Found: C, 53.09; H, 4.35; N, 10.93

This general procedure utilizing 2-(2-benzylamino-ethoxy)-4-chloro-6-nitro-phenylamine (3g) afforded:

5b N-[2-(2-Amino-5-chloro-3-nitro-phenoxy)-ethyl]-N-benzyl-2,2,2-trifluoro-acetamide as a yellow solid (76.9%), mp 106–108° C.; MS (+)FAB m/e 418/420 (M+H)$^+$.

Elemental analysis for $C_{17}H_{15}ClF_3N_3O_4$: Calc'd: C, 48.88; H, 3.62; N, 10.06 Found: C, 48.96; H, 3.50; N, 10.03

Intermediate 6a

N-[2-(1,2-Diamino-benzene-3-yloxy)-ethyl]-N-benzyl-2,2,2-trifluoro-acetamide

To a mixture containing N-[2-(2-amino-3-nitro-phenyoxy)-ethyl]-N-benzyl-2,2,2-trifluoro-acetamide (5a, 0.4 g, 1.04 mmol), 10% palladium on carbon (0.1 g) in ethanol (30 mL) was slowly added a solution of hydrazine hydrate (0.6 mL) in ethanol (10.0 mL). The mixture was heated to 55–60° C. and stirred at that temperature for 1 hr. The mixture was cooled to 25° C., filtered and the catalyst was washed with ethanol. The filtrate was concentrated under vacuum and the residue was diluted with ethyl acetate (100 mL). The organic layer was washed with water (2X, 100 mL) and brine (100 mL), dried over anhydrous magnesium sulfate, filtered, and the solvent removed under vacuum to give 0.32 g (87.5% crude yield) of product as a brown viscous oil; MS (+)FAB m/e 354 (M+H)$^+$.

This general procedure utilizing N-[2-(2-amino-5-chloro-3-nitro-phenoxy)-ethyl]-N-benzyl-2,2,2-trifluoro-acetamide (5b) afforded:

6b N-Benzyl-N-[2-(2,3-diamino-5-chloro-phenoxy)-ethyl]-2,2,2-trifluoro-acetamide as a brown viscous oil (91.3%); MS EI m/e 387/389 (M$^+$).

Elemental analysis for $C_{17}H_{117}ClF_3N_3O_2$: Calc'd: C, 52.65; H, 4.42; N, 10.84 Found: C, 52.47; H, 4.39; N, 10.90

Intermediate 7

4-Chloro-2-(2-chloro-ethoxy)-6-nitro-phenylamine

A solution of 2-(2-chloro-ethoxy)-6-nitro-phenylamine (2a, 30.0 g, 0.14 mol), N-chlorosuccinamide and acetonitrile (1.3 L) was refluxed for 4 hr. The mixture was concentrated under vacuum and the residue was diluted with ethyl acetate (500 mL). The organic layer was washed with water (2X, 250 mL) and brine (250 mL), dried over anhydrous magnesium sulfate, filtered, and the solvent removed under vacuum to give an orange solid residue. Crystallization from ethyl acetate-hexane gave 33.5 g (95.3%) as orange solid, mp 109–110° C.; MS EI m/e 250/252/254 (M$^+$).

Elemental analysis for $C_8H_8Cl_2N_2O_3$: Calc'd: C, 38.27; H, 3.21; N, 11.16 Found: C, 38.15; H, 3.10; N, 10.96

EXAMPLE 1

[2-(1H-Benzoimidazol-4-yloxy)-ethyl]-benzyl-amine

A solution of 4-(2-chloroethoxy)-benzimidazole (1, 0.39 g, 1.98 mmol) and benzylamine (9 mL) was heated at 100–110° C. for 3.5 hr. The solvent was concentrated under vacuum (50–60° C./0.1 mm), poured into 1 N sodium hydroxide (50 mL) and extracted with ethyl acetate (2X, 50 mL). The combined organic layer was washed with water (100 mL) and brine (100 mL), dried over anhydrous magnesium sulfate, filtered, and the solvent removed under vacuum to give 0.58 g of a viscous yellow oil. Purification by chromatography (60 g silica gel, methylene chloride-0.5% 2 M $NH_3$ in methanol) afforded 0.364 g (68.7%) of a yellow oil. This material was dissolved in as ethyl acetate-methanol mixture and treated with as excess amount of hydrogen chloride to give the title compound (0.38 g, 58.5%) as a white solid, mp 256–259° C. decomposed; MS EI m/e 267 ($M^+$).

Elemental analysis for $C_{16}H_{17}N_3O \cdot 2HCl \cdot 0.5\ H_2O$: Calc'd: C, 55.02; H, 5.77; N, 12.03 Found: C, 55.26; H, 5.69; N, 12.03

EXAMPLE 2

Benzyl-[2-(2-methyl-1H-benzoimidazol-4-yloxy)-ethyl]-amine

A solution of 3-(2-benzylamino-ethoxy)-benzene-1,2-diamine (4a, 0.35 g, 1.36 mmol) and acetic acid (10 mL) was refluxed for 14 hr. The solvent was concentrated under vacuum (50–60° C./0.1 mm) and the residue was dissolved in ethyl acetate (50 mL). The organic layer was washed with 1 N sodium hydroxide (50 mL), water (100 mL) and brine (100 mL), dried over anhydrous magnesium sulfate, filtered, and the solvent removed under vacuum to give crude base. Purification by chromatography (35 g silica gel, ethyl acetate-1% 2 M $NH_3$ in methanol) afforded 0.29 g (76.3%) of pure base as a tan-colored solid foam. This material was dissolved in as ethyl acetate-methanol mixture and treated with as excess amount of 1N hydrogen chloride to give the title compound (0.33 g, 90.0%) as a white solid, mp >250° C.; MS EI m/e 281 ($M^+$).

Elemental analysis for $C_{17}H_{19}N_3O \cdot 2HCl$: Calc'd: C, 57.63; H, 5.97; N, 11.61 Found: C, 57.23; H, 5.89; N, 12.86

EXAMPLE 3

Benzyl-[2-(2-trifluoromethyl-1H-benzoimidazol-4-yloxy)-ethyl]-amine

A solution of N-[2-(1,2-diamino-benzene-3-yloxy)-ethyl]-N-benzyl-2,2,2-trifluoro-acetamide (6a, 1.0 g, 2.83 mmol) and trifluoroacetic acid (10 mL) was refluxed for 4 hr. The solvent was concentrated under vacuum (50–60° C./0.1 mm) and the residue was dissolved in ethyl acetate (150 mL). The organic layer was washed with 1 N sodium hydroxide (50 mL), water (100 mL) and brine (100 mL), dried over anhydrous magnesium sulfate, filtered, and the solvent removed under vacuum to give a viscous oil residue[1]. Purification by chromatography (140 g silica gel, ethyl acetate-hexane-2 M $NH_3$ in methanol (10:10:1) afforded 0.86 g (70.7%) of N-benzyl-2,2,2-trifluoro-N-[2-(trifluoroethyl-1H-benzoimidazol-4-yloxy)-ethyl]-acetamide as a tan-colored solid foam; MS EI m/e 431 ($M^+$).

A mixture of N-benzyl-2,2,2-trifluoro-N-[2-(trifluoromethyl-1H-benzoimidazol-4-yloxy)-ethyl]-acetamide (0.78 g, 1.80 mmol), 6% aqueous methanol (35 mL) and potassium carbonate (1.7 g) was refluxed for 3 hr. The mixture was cooled to 25° C., poured into water (200 mL) and extracted with ethyl acetate (3X 150 mL). The organic layer was washed with water (200 mL) and brine (200 mL), dried over anhydrous magnesium sulfate, filtered, and the solvent removed under vacuum to give a solid residue. Crystallization of this material from ethyl acetate afforded 0.50 g (83.5%) of benzyl-[2-(2-trifluoromethyl-1H-benzoimidazol-4-yloxy)-ethyl]-amine·0.25 ethyl acetate as a white solid, mp 130–131° C.; MS EI m/e 335 ($M^+$).

Elemental analysis for $C_{17}H_{16}F_3N_3O \cdot 0.25\ C_4H_8O_2$: Calc'd: C, 60.50; H, 5.08; N, 11.76 Found: C, 60.54; H, 4.95; N, 11.72

Benzyl-[2-(2-trifluoromethyl-1H-benzoimidazol-4-yloxy)-ethyl]-amine·0.25 ethyl acetate (0.40 g, 2.61 mmol) was dissolved in as ethyl acetate-methanol mixture and treated with as excess amount of 1N hydrogen chloride to give the title compound (0.35 g, 79.1%) as a white solid, mp 194–195° C.; MS EI m/e 335 ($M^+$).

Elemental analysis for $C_{17}H_{19}N_3O \cdot HCl$: Calc'd: C, 57.63; H, 5.97; N, 11.61 Found: C, 57.23; H, 5.89; N, 12.86

EXAMPLE 4

(4-Methyl-benzyl)-[2-(2-trifluoromethyl-1H-benzoimidazol-4-yloxy)-ethyl]-amine

The general procedures used in example 2 utilizing 3-[2-(4-methyl-benzylamino)-ethoxy]-benzene-1,2-diamine (4b) and trifluoroacetic acid afforded:

(4-Methyl-benzyl)-[2-(2-trifluoromethyl-1H-benzoimidazol-4-yloxy)-ethyl]-amine 0.25 ethyl acetate as a white solid (60.5%), mp 154–158° C.; MS EI m/e 349 ($M^+$).

Elemental analysis for $C_{18}H_{18}F_3N_3O \cdot 0.25\ C_4H_8O_2$: Calc'd: C, 61.45; H, 5.43; N, 11.31 Found: C, 61.47; H, 5.40; N, 11.27

(4-Methyl-benzyl)-[2-(2-trifluoromethyl-1H-benzoimidazol-4-yloxy)-ethyl]-amine dihydrochloride as a white solid (90.1%), mp 230–233° C.; MS EI m/e 349 ($M^+$).

Elemental analysis for $C_{18}H_{18}F_3N_3O \cdot 2\ HCl$: Calc'd: C, 51.20; H, 4.77; N, 9.95 Found: C, 50.92; H, 4.69; N, 9.89

EXAMPLE 5

[2-(2-Benzyl-1H-benzoimidazol-4-yloxy)-ethyl]-(4-methyl-benzyl)-amine

The general procedures used in example 2 utilizing 3-[2-(4-methyl-benzylamino)-ethoxy]-benzene-1,2-diamine (4b) and phenylacetic acid afforded:

[2-(2-Benzyl-1H-benzoimidazol-4-yloxy)-ethyl]-(4-methyl-benzyl)-amine dihydrochloride as a white solid (65.8%), mp >250° C.; MS EI m/e 371 ($M^+$).

Elemental analysis for $C_{24}H_{25}N_3O \cdot 2\ HCl$: Calc'd: C, 64.86; H, 6.12; N, 9.46 Found: C, 64.43; H, 6.15; N, 9.31

EXAMPLE 6

(4-Methyl-benzyl)-{2-[2-(1,1,2,2,2-pentafluoro-ethyl)-1H-benzoimidazol-4-yloxy]-ethyl}-amine The general procedures used in example 2 utilizing 3-[2-(4-methyl-benzylamino)-ethoxy]-benzene-1,2-diamine (4b) and pentafluoropropionic acid afforded:

(4-Methyl-benzyl)-{2-[2-(1,1,2,2,2-pentafluoro-ethyl)-1H-benzoimidazol-4-yloxy]-ethyl}-amine 1.25 hydrate as a white solid (75.3%) mp 85–90° C. decomposed; MS EI m/e 399 ($M^+$).

Elemental analysis for $C_{19}H_{18}F_5N_3O \cdot 1.25\ H_2O$: Calc'd: C, 54.09; H, 4.90; N, 9.96 Found: C, 53.83; H, 4.65; N, 9.76

(4-Methyl-benzyl)-{2-[2-(1,1,2,2,2-pentafluoro-ethyl)-1H-benzoimidazol-4-yloxy]-ethyl}-amine hydrochloride as a white solid (79.7%) mp 180° C. decomposed; MS EI m/e 399 ($M^+$).

Elemental analysis for $C_{19}H_{18}F_5N_3O \cdot HCl$: Calc'd: C, 52.36; H, 4.39; N, 9.64 Found: C, 52.23; H, 4.31; N, 9.54

EXAMPLE 7

Thiophen-2-ylmethyl-[2-(2-trifluoromethyl-1H-benzoimidazol-4-yloxy)-ethyl]-amine The general procedures used in example 2 utilizing 3-{2-[(thiophen-2-ylmethyl)-amino]-ethoxy}-benzene-1,2-diamine (4c) and trifluoroacetic acid afforded:

Thiophen-2-ylmethyl-[2-(2-trifluoromethyl-1H-benzoimidazol-4-yloxy)-ethyl]-amine 1.6 Hydrochloride as a tan solid (58.3%), mp 184° C.; MS EI m/e 341 (M⁺).

Elemental analysis for $C_{18}H_{18}F_3N_3O \cdot 1.6$ HCl: Calc'd: C, 44.98; H, 4.04; N, 10.38 Found: C, 44.99; H, 4.05; N, 10.33

EXAMPLE 8

Benzyl-[3-(2-trifluoromethyl-1H-benzoimidazol-4-yloxy)-propyl]-amine

The general procedures used in example 2 utilizing 3-(3-benzylamino-propoxy)-benzene-1,2-diamine (4f) and trifluoroacetic acid afforded:

Benzyl-[3-(2-trifluoromethyl-1H-benzoimidazol-4-yloxy)-propyl]-amine hemi hydrate as a tan solid foam (57.6%), mp 50–70° C.; MS EI m/e 349 (M⁺).

Elemental analysis for $C_{18}H_{18}F_3N_3O \cdot 0.5$ $H_2O$: Calc'd: C, 60.33; H, 5.34; N, 11.73 Found: C, 60.34; H, 5.30; N, 11.84

Benzyl-[3-(2-trifluoromethyl-1H-benzoimidazol4-yloxy)-propyl]-amine Dihydrochloride as a white solid (98.0%), mp 194–197° C.; MS EI m/e 349 (M⁺).

Elemental analysis for $C_{18}H_{18}F_3N_3O \cdot 2$ HCl: Calc'd: C, 51.20; H, 4.77; N, 9.95 Found: C, 51.09; H, 4.49; N, 9.86

EXAMPLE 9

Benzyl-{2-[2-(1,1,2,2,2-pentafluoro-ethyl)-1H-benzoimidazol-4-yloxy]-ethyl}-amine The general procedures used in example 3 utilizing N-[2-(1,2-diamino-benzene-3-yloxy)-ethyl]-N-benzyl-2,2,2-trifluoro-acetamide (6a) and pentafluoropropionic acid afforded:

Benzyl-{2-[2-(1,1,2,2,2-pentafluoro-ethyl)-1H-benzoimidazol-4-yloxy]-ethyl}-amine as a white solid (59.8%), mp 152–153° C.; MS EI m/e 385 (M⁺).

Elemental analysis for $C_{18}H_{16}F_5N_3O$: Calc'd: C, 56.11; H, 4.19; N, 10.91 Found: C, 56.02; H, 4.10; N, 10.73

Benzyl-{2-[2-(1,1,2,2,2-pentafluoro-ethyl)-1H-benzoimidazol-4-yloxy]-ethyl}-amine hydrochloride 0.75 hydrate as a white solid (69.4%), mp 120–135° C.; MS (+)ESI m/e 386 (M+H⁺).

Elemental analysis for $C_{18}H_{16}F_5N_3O \cdot HCl \cdot 0.75$ $H_2O$: Calc'd: C, 49.67; H, 4.28; N, 9.65 Found: C, 49.88; H, 3.95; N, 9.66

EXAMPLE 10

Naphthalen-1-ylmethyl-[2-(2-trifluoromethyl-1H-benzoimidazol-4-yloxy)-ethyl]-amine The general procedures used in example 2 utilizing 3-{2-[(naphthalen-1-ylmethyl)-amino]-ethoxy}-benzene-1,2diamine (4d) and trifluoroacetic acid afforded:

Naphthalen-1-ylmethyl-[2-(2-trifluoromethyl-1H-benzoimidazol-4-yloxy)-ethyl]-amine as a white solid (63.1%), mp 130–133° C.; MS EI 385 m/e (M⁺).

Elemental analysis for $C_{21}H_{18}F_3N_3O$: Calc'd: C, 65.45; H, 4.71; N, 10.90 Found: C, 65.28; H, 4.43; N, 10.57

Naphthalen-1-ylmethyl-[2-(2-trifluoromethyl-1H-benzoimidazol4-yloxy]-ethyl]-amine hydrochloride as a white solid (94.8%), mp 208–209° C.; MS EI m/e 385 (M⁺).

Elemental analysis for $C_{18}H_{18}F_3N_3O \cdot HCl$: Calc'd: C, 59.79; H, 4.54; N, 9.96 Found: C, 59.39; H, 4.45; N, 9.81

EXAMPLE 11

Thiophen-2-ylmethyl-[2-(1H-benzoimidazol-4-yloxy)-ethyl]-amine

The general procedures used in example 2 utilizing 3-{2-[(thiophen-2-ylmethyl)-amino]-ethoxy}-benzene-1,2-diamine (4c) and formic acid afforded:

Thiophen-2-ylmethyl-[2-(1H-benzoimidazol-4-yloxy)-ethyl]-amine quarter hydrate as a viscous yellow oil (63.2%); MS EI m/e 273 (M⁺).

Elemental analysis for $C_{14}H_{15}N_3OS \cdot 0.25$ $H_2O$: Calc'd: C, 60.52; H, 5.62; N, 15.12 Found: C, 60.85; H, 5.49; N, 15.39

Thiophen-2-ylmethyl-[2-(1H-benzoimidazol-4-yloxy)-ethyl]-amine dihydrochloride hemihydrate as a white solid (69.2%), mp 248–252° C. decomposed; MS EI m/e 273 (M⁺).

Elemental analysis for $C_{14}H_{15}N_3OS \cdot 2.0$ $HCl \cdot 0.5$ $H_2O$: Calc'd: C, 47.33; H, 5.11; N, 11.83 Found: C, 46.95; H, 5.13; N, 11.73

EXAMPLE 12

(4-Methyl-benzyl)-{2-[2-(1,1,2,2,3,3,3-heptafluoro-propyl)-1H-benzoimidazol-4-yloxy]-ethyl}-amine The general procedures used in example 2 utilizing 3-[2-(4-methyl-benzylamino)-ethoxy]-benzene-1,2-diamine (4b) and heptafluorobutyric acid afforded:

(4-Methyl-benzyl)-{2-[2-(1,1,2,2,3,3,3-heptafluoro-propyl)-1H-benzoimidazol-4-yloxy]-ethyl}-amine as a white solid (63.7%) mp 144–146° C.; MS EI m/e 449 (M⁺).

Elemental analysis for $C_{20}H_{18}F_7N_3O$: Calc'd: C, 53.46; H, 4.04; N, 9.35 Found: C, 53.23; H, 3.69; N, 9.11

(4-Methyl-benzyl)-{2-[2-(1,1,2,2,3,3,3-heptafluoro-propyl)-1H-benzoimidazol-4-yloxy]-ethyl}-amine 1.5 hydrochloride as a white solid (87.6%) mp 198–199.5° C.; MS EI m/e 449 (M⁺).

Elemental analysis for $C_{19}H_{18}F_5N_3O \cdot 1.5$ HCl: Calc'd: C, 47.66; H, 3.90; N, 8.34 Found: C, 47.47; H, 3.76; N, 8.24

EXAMPLE 13

2-[2-(2-Trifluoromethyl-1H-benzoimidazol-4-yloxy-ethyl]-1,2,3,4-tetrahydro-isoquinoline The general procedures used in example 2 utilizing 3-[2-(3,4-dihydro-1H-isoquinolin-2-yl)-ethoxy]-benzene-1,2-diamine (4e) and trifouoroacetic acid afforded:

2-[2-(2-Trifluoromethyl-1H-benzoimidazol-4-yloxy)-ethyl]-1,2,3,4-tetrahydro-isoquinoline quarter hydrate as a white solid (95.8%) mp 168–171° C.; MS EI m/e 361 (M⁺).

Elemental analysis for $C_{19}H_{18}F_3N_3O \cdot 0.25$ $H_2O$: Calc'd: C, 62.37; H, 5.10; N, 11.49 Found: C, 62.52; H, 4.85; N, 11.50

2-[2-(2-Trifluoromethyl-1H-benzoimidazol-4-yloxy)-ethyl]-1,2,3,4-tetrahydro-isoquinoline dihydrochloride as a white solid (94.3%) mp 210–214° C. decomposed; MS EI m/e 361 (M⁺).

Elemental analysis for $C_{19}H_{18}F_3N_3O \cdot 2$ HCl: Calc'd: C, 52.55; H, 4.64; N, 9.68 Found: C, 52.20; H, 4.81; N, 9.33

EXAMPLE 14

Benzyl-[2-(6-chloro-2-trifluoromethyl-1H-benzoimidazol-4-yloxy)-ethyl]-amine

The general procedures used in example 3 utilizing N-benzyl-N-[2-(2,3-diamino-5-chloro-phenoxy)-ethyl]-2,2,2-trifluoro-acetamide (6b) and trifluoroacetic acid afforded:

Benzyl-[2-(6-chloro2-trifluoromethyl-1H-benzoimidazol-4yloxy)-ethyl]-amine as a white solid (76.4%), mp 171–172° C.; MS EI m/e 369 (M+).

Elemental analysis for $C_{17}H_{15}ClF_3N_3O$: Calc'd: C, 55.22; H, 4.09; N, 11.36 Found: C, 55.05; H, 3.91; N, 11.13

Benzyl-[2-(6-chloro-2-trifluoromethyl-1H-benzoimidazol-4-yloxy)-ethyl]-amine as a white solid (73.4%), mp 210–212° C.; MS EI m/e 369 (M+).

Elemental analysis for $C_{17}H_{15}ClF_3N_3O \cdot HCl$: Calc'd: C, 50.26; H, 3.97; N, 10.34 Found: C, 50.29; H, 3.81; N, 10.32

EXAMPLE 15

4-Chloro-benzyl-[2-(6-chloro-2-trifluoromethyl-1H-benzoimidazol-4-yloxy)-ethyl]-amine The general procedures used in example 2 utilizing 3-[2-(4-chloro-benzylamino)-ethoxy]-4-chloro-benzene-1,2-diamine (4g) and trifluoroacetic acid afforded:

4-Chloro-benzyl-[2-(6chloro-2-trifluoromethyl-1H-benzoimidazol-4-yloxy)-ethyl]-amine fumatate as a light-gray colored solid (79.6%), np 191–193° C. MS EI m/e 403/405/407 (M+).

Elemental analysis for $C_{17}H_{14}Cl_3F_3N_3O \cdot C_4H_4O_4$: Calc'd: C, 48.48; H, 3.49; N, 8.08 Found: C, 48.17; H, 3.26; N, 8.11

EXAMPLE 16

(4-Fluoro-benzyl)-2[2-(2-trifluoromethyl-1H-benzoimidazol-4-yloxy)-ethyl]-amine

The general procedures used in example 2 utilizing 3-[2-(4-fluoro-benzylamino)-ethoxy]-benzene-1,2-diamine (4h) and trifluoroacetic acid afforded:

(4-Fluoro-benzyl)-2[2-(2-trifluoromethyl-1H-benzoimidazol-4-yloxy)-ethyl]-amine hydrochloride hemihydrate as a white solid (50.4%), mp 225–227° C.; MS EI m/e 353 (M+).

Elemental analysis for $C_{17}H_{15}F_4N_3O \cdot 1.0$ HCl$\cdot 0.5$ H$_2$O: Calc'd: C, 51.20; H, 4.30; N, 10.54 Found: C, 51.06; H, 3.93; N, 10.35

EXAMPLE 17

[2-(2-Trifluoromethyl-1H-benzoimidazol-4-yloxy)-ethyl]-(4-trifluoromethyl-benzyl)-amine The general procedures used in example 2 utilizing 3-[2-(4-trifluoromethyl-benzylamino)-ethoxy]-benzene-1,2-diamine (4i) and trifluoroacetic acid afforded:

[2-(2-Trifluoromethyl-1H-benzoimidazol-4-yloxy)-ethyl]-(4-trifluoromethyl-benzyl)-amine hydrochloride as a white solid (80.5%), mp 188–190° C.; MS (+)FAB m/e 404 (M+H+).

Elemental analysis for $C_{18}H_{15}F_6N_3O \cdot 1.0$ HCl: Calc'd: C, 49.16; H, 3.67; N, 9.55 Found: C, 49.21; H, 3.50; N, 9.46

EXAMPLE 18

(3-Phenyl-propyl)-[2-(2-trifluoromethyl-1H-benzoimidazol-4-yloxy)-ethyl]-amine

The general procedures used in example 2 utilizing 3-[2-(3-phenyl-propylamino)-ethoxy]-benzene-1,2-diamine (4j) and trifluoroacetic acid afforded:

(3-Phenyl-propyl)-[2-(2-trifluoromethyl-1H-benzoimidazol-4-yloxy)ethyl]-amine hydrochloride as a white solid (88.7%), mp 167–170° C.; MS (+)FAB m/e 364 (M+H+).

Elemental analysis for $C_{19}H_{20}F_3N_3O$ 1.0 HCl: Calc'd: C, 57.07; H, 5.29; N, 10.51 Found: C, 56.89; H, 5.15; N, 10.28

PHARMACOLOGY

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the immediately following table.

| Example No. | IC$_{50}$ (nM) D$_2$ Quin. | IC$_{50}$ (nM) D$_2$ Spiper | Ratio |
|---|---|---|---|
| 1 | 26.75 | — | — |
| 2 | 8.85 | 339 | 38.3 |
| 3 | 0.36 | 23.7 | 65.8 |
| 4 | 0.74 | 29.9 | 40.4 |
| 5 | 54.8 | 2159 | 39.4 |
| 6 | 1.44 | 66.5 | 46.2 |
| 7 | 1.03 | 37.35 | 36.3 |
| 8 | 86.76 | 1456 | 16.8 |
| 9 | 1.41 | 41.88 | 29.7 |
| 10 | 0.86 | 81.5 | 94.8 |
| 11 | 52.8 | — | — |
| 12 | 5.12 | 118.0 | 23.0 |
| 13 | 8.00 | 314.4 | 39.4 |
| 14 | 1.42 | 150.5 | 106 |
| 15 | 7.77 | 395.0 | 50.8 |
| 16 | 0.74 | 49.0 | 66.2 |
| 17 | 1.16 | 87.0 | 75.0 |
| 18 | 0.56 | — | — |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:
1. A compound of formula I:

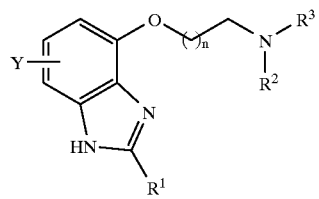

wherein:
$R^1$ is hydrogen, trifluoromethyl, pentafluoroethyl, heptafluoropropyl, straight-chain or branched alkyl group having up to 6 carbons or benzyl optionally substituted by one to three substituents selected from halogen, amino, nitro, hydroxy, and $C_1$–$C_6$ alkoxy;

$R^2$ is hydrogen or $C_1$–$C_6$ alkyl;

$R^3$ is hydrogen, straight-chain or branched alkyl group having up to 10 carbon atoms, cyclohexylmethyl, —$(CH_2)_m$Ar where Ar is phenyl, thienyl, furanyl, or pyridinyl, each optionally substituted by one to two substituents selected from halogen, $C_1$–$C_6$ alkoxy, trifluoromethyl and $C_1$–$C_6$ alkyl, and m is 1–3;

or $NR^2R^3$ is 1,2,3,4-tetrahydroquinolin-1-yl or 1,2,3,4-tetrahydroisoquinolin-2-yl;

Y is hydrogen, halogen, lower alkyl, amino, or lower alkoxy; and n is 1–5, provided, however, that where $R^1$ is aminoloweralkyl, both $R^2$ and $R^3$ may not be hydrogen, or a pharmaceutically acceptable salt thereof.

2. A compound according to claim 1 wherein $R^3$ is benzyl, substituted benzyl, thienylmethyl, furanylmethyl, phenybutyl, or cyclohexylmethyl, $R^1$ is trifluoromethyl or pentafluoroethyl; and $NR^2R^3$ tetrahydroisoquinolinyl.

3. A compound according to claim 1 which is [2-(1H-benzoimidazol4-yloxy)-ethyl]-benzyl-amine or a pharmaceutically acceptable salt thereof.

4. A compound according to claim 1 which is benzyl-[2-(2-methyl-1H-benzoimidazol-4-yloxy)-ethyl]-amine or a pharmaceutically acceptable salt thereof.

5. A compound according to claim 1 which is benzyl-[2-(2-trifluoromethyl-1H-benzoimidazol-4-yloxy)-ethyl]-amine or a pharmaceutically acceptable salt thereof.

6. A compound according to claim 1 which is (4methyl-benzyl)-[2-(2-trifluoromethyl-1H-benzoimidazol-4-yloxy)-ethyl]-amine or a pharmaceutically acceptable salt thereof.

7. A compound according to claim 1 which is [2-(2-benzyl-1H-benzoimidazol-4-yloxy)ethyl]-(4-methyl-benzyl)-amine or a pharmaceutically acceptable salt thereof.

8. A compound according to claim 1 which is (4-methyl-benzyl)-{2-[2-(1,1,2,2,2-pentafluoro ethyl)-1H-benzoimidazol-4-yloxy]-ethyl}-amine or a pharmaceutically acceptable salt thereof.

9. A compound according to claim 1 which is thiophen-2-ylmethyl-[2-(2-trifluoromethyl-1H-benzoimidazol-4yloxy)-ethyl]-amine or a pharmaceutically acceptable salt thereof.

10. A compound according to claim 1 which is benzyl-[3-(2-trifluoromethyl-1H-benzoimidazol-4-yloxy)-propyl]-amine or a pharmaceutically acceptable salt thereof.

11. A compound according to claim 1 which is benzyl-{2-[2-(1,1,2,2,2-pentafluoro-ethyl)-1H-benzoimidazol-4-yloxy]-ethyl}-amine or a pharmaceutically acceptable salt thereof.

12. A compound according to claim 1 which is naphthlene-1-ylmethyl-[2-(2-trifluoromethyl-1H-benzoimidazol-4-yloxy]-ethyl]-amine or a pharmaceutically acceptable salt thereof.

13. A compound according to claim 1 which is thiophen-2-ylmethyl-[2-(1H-benzoimidazol-4-yloxy)-ethyl]-amine or a pharmaceutically acceptable salt thereof.

14. A compound according to claim 1 which is (4-methyl-benzyl)-{2-[2-(1,1,2,2,3,3,3-heptafluoro-propyl)-1H-benzoimidazol-4-yloxy]-ethyl}-amine or a pharmaceutically acceptable salt thereof.

15. A compound according to claim 1 which is 2-[2-(2-trifluoromethyl-1H-benzoimidazol-4-yloxy-ethyl]-1,2,3,4-tetrahydro-isoquinoline or a pharmaceutically acceptable salt thereof.

16. A compound according to claim 1 which is benzyl-[2-(6-chloro-2-trifluoromethyl-1H-benzoimidazol-4-yloxy)-ethyl-amine or a pharmaceutically acceptable salt thereof.

17. A compound according to claim 1 which is 4chloro-benzyl-[2-(6chloro-2-trifluoromethyl-1H-benzoimidazol-4yloxy)-ethyl-amine or a pharmaceutically acceptable salt thereof.

18. A compound according to claim 1 which is (4-fluoro-benzyl)-2[2-(2-trifluoromethyl-1H-benzoimidazol-4-yloxy)-ethyl]-amine or a pharmaceutically acceptable salt thereof.

19. A compound according to claim 1 which is [2-(2-trifluoromethyl-1H-benzoimidazol-4-yloxy)-ethyl]-(4-trifluoromethyl-benzyl)-amine or a pharmaceutically acceptable salt thereof.

20. A compound according to claim 1 which is (3-phenyl-propyl)-[2-(2-trifluoromethyl-1H-benzoimidazol-4-yloxy)-ethyl]-amine or a pharmaceutically acceptable salt thereof.

21. A method of treating diseases in a mammal which respond to treatment with dopamine $D_2$ agonists which comprises administering to a mammal in need thereof a therapeutically effective amount of a compound of the formula

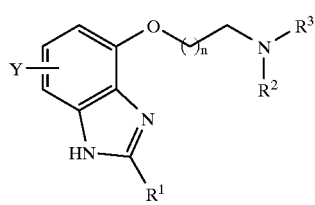

wherein:
R$^1$ is hydrogen, trifluoromethyl, pentafluoroethyl, heptafluoropropyl, straight-chain or branched alkyl group having up to 6 carbons or benzyl optionally substituted by one to three substituents selected from halogen, amino, nitro, hydroxy, and C$_1$–C$_6$ alkoxy;

R$^2$ is hydrogen or C$_1$–C$_6$ alkyl;

R$^3$ is hydrogen, straight-chain or branched alkyl group having up to 10 carbon atoms, cyclohexylmethyl or —(CH$_2$)$_m$Ar where Ar is phenyl, naphthalenyl, thienyl, furanyl, or pyridinyl, each optionally substituted by one to two substituents selected from halogen, C$_1$–C$_6$ alkoxy, trifluoromethyl and C$_1$–C$_6$ alkyl, and m is 1–3;

or NR$^2$R$^3$ is 1,2,3,4-tetrahydroquinolin-1-yl or 1,2,3,4-tetrahydroisoquinolin-2-yl;

Y is hydrogen, halogen, lower alkyl, amino, or lower alkoxy; and n is 1–5, or a pharmaceutically acceptable salt thereof.

22. The method of treatment according to claim 21 wherein the disease treated is schizophrenia.

23. The method of treatment according to claim 21 wherein the disease treated is Parkinson's disease.

24. The method of treatment according to claim 21 wherein the disease treated is Tourette's syndrome.

25. The method of treatment according to claim 21 wherein the disease treated is drug or alcohol addiction.

26. A pharmaceutical composition which comprises a pharmaceutically acceptable carrier and a therapeutically effective amount of a compound of the formula

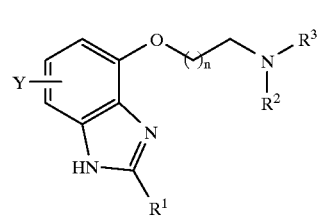

wherein:
R$^1$ is hydrogen, trifluoromethyl, pentafluoroethyl, heptafluoropropyl, straight-chain or branched alkyl group having up to 6 carbons or benzyl optionally substituted by one to three substituents selected from halogen, amino, nitro, hydroxy, and C$_1$–C$_6$ alkoxy;

R$^2$ is hydrogen or C$_1$–C$_6$ alkyl;

R$^3$ is hydrogen, straight-chain or branched alkyl group having up to 10 carbon atoms, cyclohexylmethyl or —(CH$_2$)$_m$Ar where Ar is phenyl naphthalenyl, thienyl, furanyl, or pyridinyl, each optionally substituted by one to two substituents selected from halogen, C$_1$–C$_6$ alkoxy, trifluoromethyl and C$_1$–C$_6$ alkyl, and m is 1–3;

or NR$^2$R$^3$ is 1,2,3,4-tetrahydroquinolin-1-yl or 1,2,3,4-tetrahydroisoquinolin-2-yl;

Y is hydrogen, halogen, lower alkyl, amino, or lower alkoxy; and n is 1–5, provided, however, that where R$^1$ is aminoloweralkyl, both R$^2$ and R$^3$ may not be hydrogen.

or a pharmaceutically acceptable salt thereof.

* * * * *